(12) United States Patent  
Paradis

(10) Patent No.: US 6,168,137 B1  
(45) Date of Patent: Jan. 2, 2001

(54) SWABBABLE CHECK VALVE

(76) Inventor: Joseph R. Paradis, Box 22238, Hilton Head Island, SC (US) 29925

( * ) Notice: Under 35 U.S.C. 154(b), the term of this patent shall be extended for 0 days.

(21) Appl. No.: 08/777,081

(22) Filed: Dec. 30, 1996

Related U.S. Application Data

(63) Continuation-in-part of application No. 08/777,081, filed on Dec. 30, 1996.

(51) Int. Cl.$^7$ ............................. F16L 37/00; A61M 5/00

(52) U.S. Cl. ................................ 251/149.6; 251/149.1; 604/249; 604/256

(58) Field of Search ......................... 251/149.6, 149.1, 251/149.3, 149.5, 149; 604/167, 249, 256, 905, 283, 169

(56) References Cited

U.S. PATENT DOCUMENTS

| | | | |
|---|---|---|---|
| 3,285,298 | * 11/1966 | Gellman | 251/149.1 X |
| 3,352,531 | * 11/1967 | Kilmarx | 251/149.6 |
| 4,411,287 | * 10/1983 | Hyde | 251/149.6 X |
| 5,776,113 | * 7/1998 | Daugherty et al. | 251/149.6 |

* cited by examiner

*Primary Examiner*—Kevin Lee  
(74) *Attorney, Agent, or Firm*—G. Kersey

(57) ABSTRACT

An apparatus comprises a housing having an end with an input having an entrance and an output and a probe integral with the housing extending from the output to beyond the end of the input. The probe has a passageway connected to the output. A spring-biased seal is disposed about the probe to seal the passageway and is depressible by an exterior member to expose the passageway. The extension of the probe beyond the end of the input permits the swabbing thereof before the depression of the seal.

15 Claims, 4 Drawing Sheets

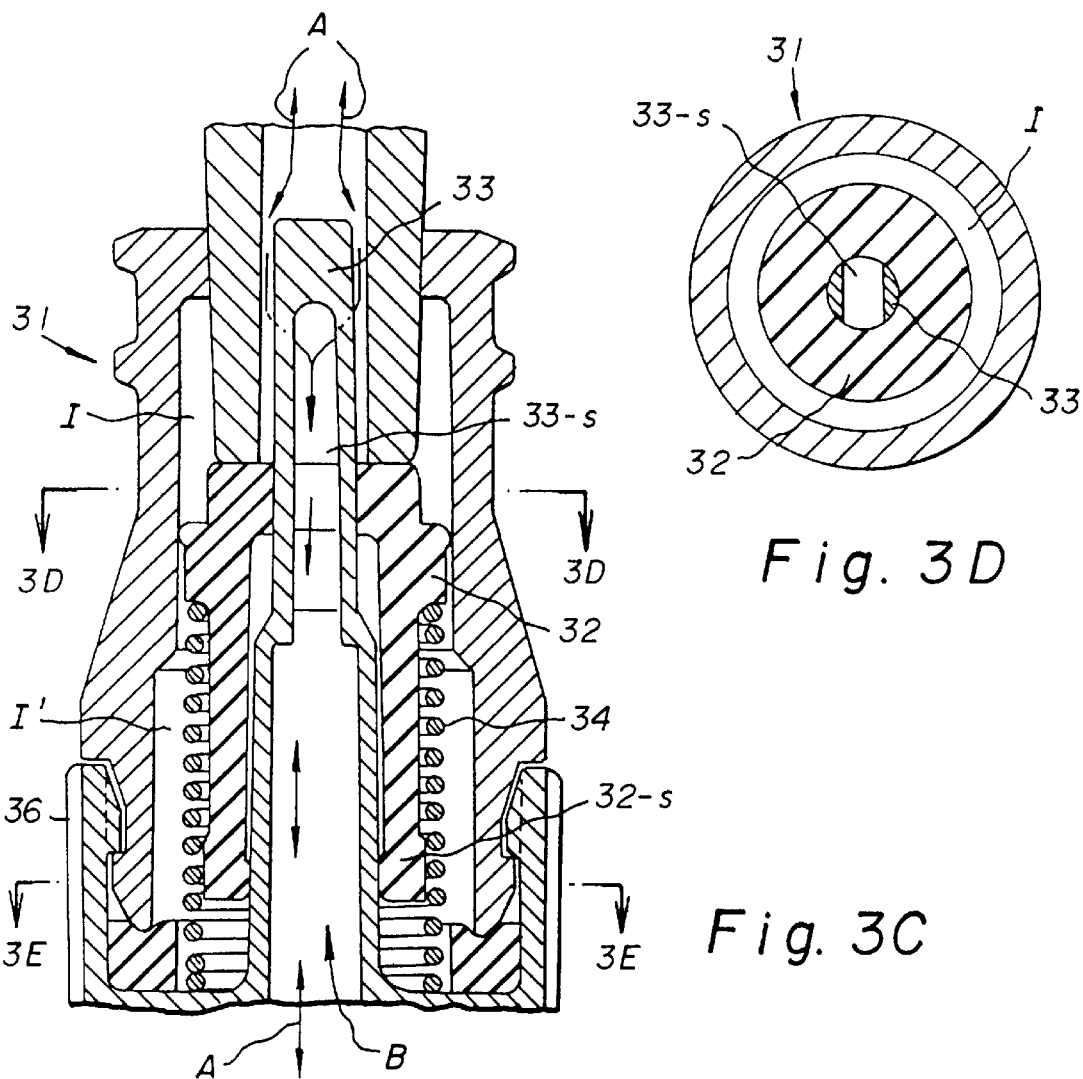
Fig. 3C
Fig. 3D
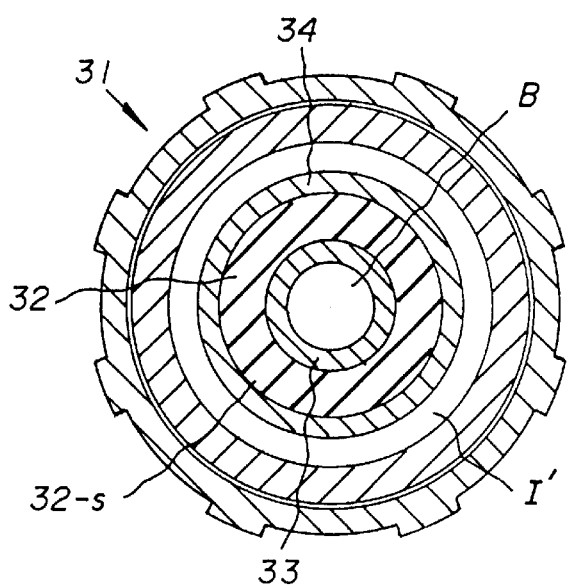
Fig. 3E

SWABBABLE CHECK VALVE

This is a file wrapper continuation-in-part of application Ser. No. 08/777,081 filed Dec. 30, 1996.

BACKGROUND OF THE INVENTION

The invention relates to flow control and, more particularly, to swabbable check valves for the needless control of injected fluids.

A valve is a device that regulates flow. A check valve permits flow in one direction only. Where fluids need to be introduced into the body, it is common practice to do so through a check valve connected to a catheter, which is a slender hollow tube inserted into a body passage or cavity for passing fluids.

For example, medication can be injected into a check valve connected to a catheter. In prior practice, medication from the syringe has been introduced using a needle, but this can be undesirable, since in modern medical practice, needle sticks are to be avoided. A number of attempts have been made to achieve the introduction of medication without the need for using syringes with needles.

Illustrative examples of attempted needless control of injected fluids are disclosed in Newgard et al., U.S. Pat. No. 5,064,416; Sivert, U.S. Pat. No. 4,915,687; Jackson, U.S. Pat. No. 4,429,856; Kilmarx, U.S. Pat. No. 3,352,531 and Faust et al. U.S. Pat. No. 5,116,021. All of these illustrative arrangements have the objection that pathogens can enter their inlets without being easily sterilized. While attempts have been made to maintain sterility by capping the inlets, the requirement of caps presents additional complexity and expense. In addition, caps can become dislodged during storage and handling, rending the devices unusable or requiring special sterilization procedures.

Newgard '416 is typical in having a long inlet passage before there is access to a moveable member which is pierceable and controls flow by the extent to which a valving member can be dilated. Sivert, Johnson, Kilmarx and Faust are similarly objectionable.

Still another consideration is desire to operate flow control devices with low "cracking" pressures, i.e. the pressure at which a control member moves away from its seat. For such devices, it is desirable to use relatively thin diaphragms. Unfortunately, thin diaphragms pose problems of stability. The diaphragm may move slightly away from its central position and become lodged against a side wall, causing a problem of leakage.

The catheters used with check valves are of various types. One type includes a tubular member for the introduction of fluids into a blood channel which may be venous or arterial. Another type is a double-walled flexible tube which terminates at its outer end in two separate branches. One branch continues as an outer tube and terminates at its inner end in a inflatable portion. The other branch continues as an inner tube with a through passage that extends to the inflatable portion of the outer tube. There are various other types of catheters as well.

With all types of catheters, it is desirable to be able to control the through flow of fluid using a suitable valve, which can be used in non-catheter applications as well.

Accordingly, it is an object of the invention to provide a miniature check valve which can be used without needles and is swabbable by being easily wiped with disinfectant across its inlet to eliminate contamination and pathogens. A related object is to allow the check valve to be readily usable with devices, such as catheters, to control fluid flow while restricting operation by a patient or unauthorized personnel.

A further object of the invention is to provide a simple and expendable check valve, which can be mass produced, readily assembled and provide ease of operation.

SUMMARY OF THE INVENTION

In accomplishing the foregoing and related objects a miniature check valve is provided by a tubular housing having centered at its inlet bore a solid-ended and non-moveable probe surrounded by an annular sealing member so that both the probe and the sealing member can be cleansed by swabbing, i.e., wiping, the inlet end before the annular sealing member is depressed by, for example, the blunt end of a syringe in order to engage an internal passageway of the probe and permit passage of fluid from the syringe through the valve.

The sealing member abuts an inwardly facing shoulder or valve seat, and is held in its closed position by, for example, a spring, which can be elastomeric, until the sealing member is disengaged from the valve seat by an external member, such as the hollow blunt end of a syringe containing fluid that is to be injected through the valve, for example, into a catheter.

In accordance with a broad aspect of the invention, the housing has an input and output; a probe within the housing extends from the output to beyond the input; the probe has a passageway thereinto connected to the output; and a depressible member seals the input, surrounding the probe and being depressible therealong to expose the passageway.

Because of the extension of the probe beyond the input swabbing of the probe is permitted before the depression of the sealing member.

The input has an entrance and the sealing means can be substantially flush with the entrance. Where the entrance has a prescribed level, the sealing member can terminate at the prescribed level, or below it.

The probe is configured to facilitate contact with an external member, such as a Luer fitting for depressing the sealing member. The probe can terminate in a rounded end beyond the input or in a flattened end.

The sealing member seals to the housing and to the probe, and the sealing to probe can be at a plurality of positions therealong. The sealing member can include provision for applying spring force thereto.

In a method of the invention the steps include: sealing an input by a depressible member surrounding a probe extending beyond the input; and depressing the member to uncover, in the probe, a passageway connected to an output. As a result, the depression of the member permits flow from the input to the output.

The member is depressible from a position substantially flush with the entrance to the input. Where the entrance has a prescribed level, the member is depressible from the prescribed level, or from below the prescribed level.

The method further includes the step of contacting the probe by an outside member, such as a Luer termination, for depressing the sealing member. The step of contacting the probe takes place at a rounded end beyond the input, or astride a flattened end beyond the input.

The sealing to the probe can be at a plurality of different locations therealong, spring force can be applied to the sealing member.

In a method of manufacturing a swabbable check valve the steps include: (a) providing a housing having an input and containing a probe within the housing extending from a output to beyond the input; (b) proving, into the probe, a passageway that is connected to the output; and (c) sealing the input by a member surrounding the probe and depressible therealong to expose the passageway. The extension of the probe beyond the input permits the swabbing thereof before the depression of the sealing member.

A miniature check valve in accordance with the invention includes a tubular housing having an outlet and an inlet at a level surrounded by an exterior surface; a bore extending from the exterior surface into the housing; a stationary probe centered at the inlet at the level of the exterior surface, with the probe having an internal channel extending to the outlet, and a passageway at a position where there is communication outwardly from the interior channel; and there is an annular member between the probe and the interior of the housing for sealing the inlet, with the annular member being depressible to the position of the passageway in the stationary probe. Because of the location of the probe and the annular member relative to the inlet easy swabbing across the inlet and exterior surface is facilitated. Swabbing is further facilitated where the annular member is flush with the inlet.

The apparatus of the invention encompasses means having an exterior surface at a level containing an inlet; means centered in the inlet at the level of the exterior surface and having a passageway for communicating with the inlet and extending to an interior channel for communicating with an outlet; and means depressible at the inlet to the position of the passageway; whereby the exterior surface, the depressible member and the channel containing member can be swabbed to reduce contamination and pathogens before the depressible member is depressed.

The housing of the invention has an interior with a bore extending from an inlet into the housing; a stationary probe is centered in the housing and included in any hypothetical extension of the inlet surface; the probe has exterior and an interior channel extending to the outlet, with a passageway communicating between the interior channel and the exterior of the probe; and an annular member between the probe and the interior of the housing seals the inlet and is depressible to the position of the passageway in the probe.

DESCRIPTION OF THE DRAWINGS

Other aspects of the invention will become apparent after considering several illustrative embodiments taken in conjunction with the drawings in which:

FIG. 3C is a expanded sectional view of the valve and Luer actuator end of FIG. 3A showing the depression of the Luer end into the bore of the swabbable check valve;

FIG. 3D is a sectional view of FIG. 3C, taken along the lines 3D—3D, illustrating a portion of the flow channel;

FIG. 3E is a sectional view of FIG. 3C, taken along the lines 3E—3E, illustrating the further aspects of sealing.

DETAILED DESCRIPTION

Figure 1A:
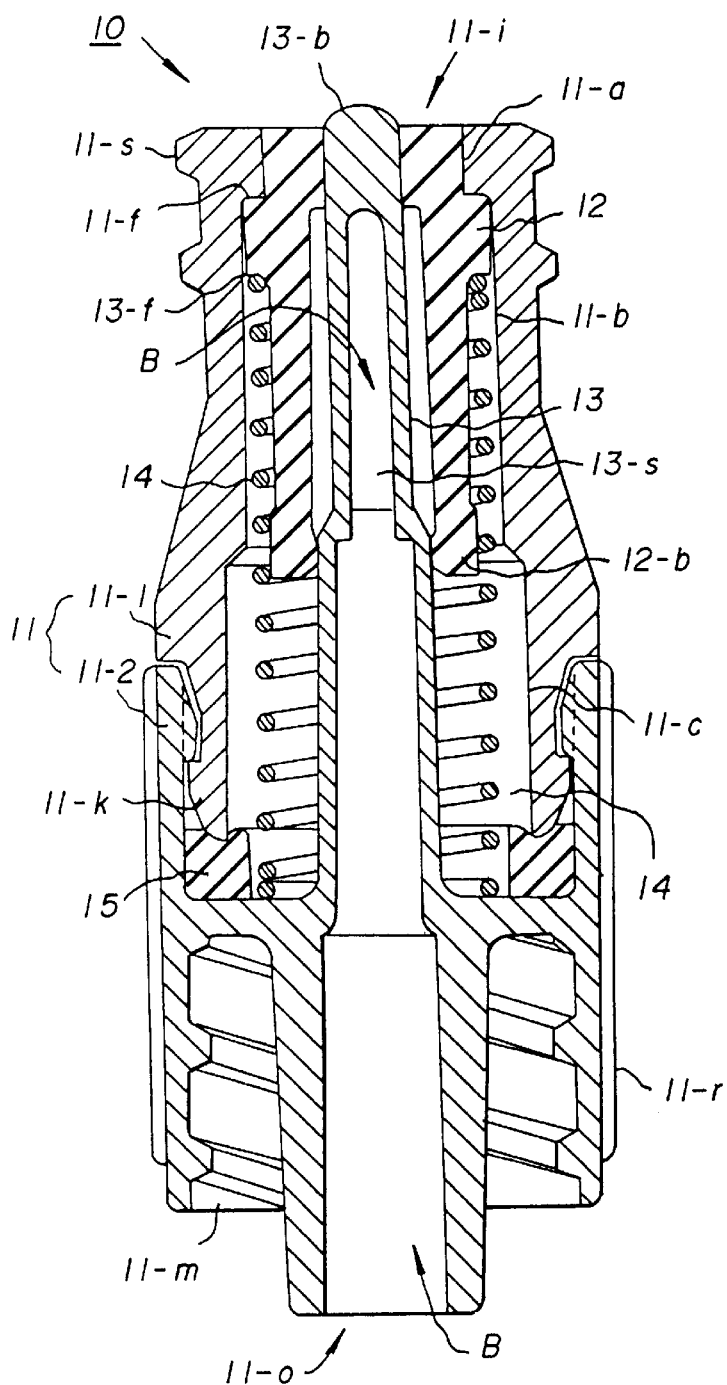
FIG. 1A is an enlarged section, taken along a diameter, through a swabbable check valve embodying the invention.

With reference to the drawings, the check valve 10 of FIG. 1A includes a tubular housing 11 with two parts 11-1 and 11-2. The part 11-1, which occupies an "upper" position in FIG. 1A, contains an annular sealing member 12 that surrounds the upper portion of a stationary probe 13. The probe 13 is centered in the bore B of the housing 11 and contains an axial slot 13-s that extends to an outlet 11-o of the housing 11.

The upper portion of the sealing member 12, below the inlet 11-i of the housing 11, slidably engages the upper end of the probe 13, while the intermediate portion of the sealing member 12, adjoining the slot 13-s, is spaced from the probe 13, which returns to sealing engagement with the member 12 at its base 12-b.

A closed and blunt end 13-b of the probe 13 is elevated above the valve inlet 11-i to serve as a locator for an external member by which the sealing member 12 is depressible, as explained below. The sealing member 12 is held in its operative sealing position against a bore flange 11-f by a helical spring 14 acting against a flange 13-f of the sealing member 13.

The parts 11-1 and 11-2 of tubular housing 11 are joined together by a snap lock 11-k, with the upper part 11-1 in contact with a circumferential seal 15 that is supported by the lower part 11-2. The bore B of the housing upper part 11-1 has portions 11a, 11b and 11c, of different diameters. The bore portion 11a serves as a female Luer inlet and has its walls tapered accordingly. The portion 11b is enlarged to accommodate the main body of the sealing member 12, which is surrounded by the spring 14 and thus supports the seal 12-b, while the portion 11c accommodates the compression of the spring 14.

Figure 1B:
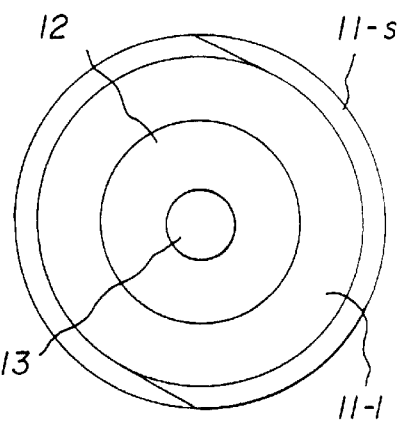
FIG. 1B is a top view of the swabbable check valve of FIG. 1A before sectioning.

The exterior of the housing 11 is provided at its inlet end 11-i, also shown in FIG. 1B, with threads 11-s and has a a male Luer 11-m at its outlet end 11-o. The portion 11-2 has ribs 11-r. The functions of the threads 11-s and the male Luer 11-m will presently become apparent. The housing may be formed of any suitable material, such as an elastomer or synthetic resin capable of being formed or molded.

Figure 1C:
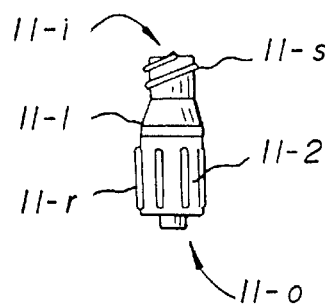
FIG. 1C is a full-scale view of the swabbable check valve of FIG. 1A, with its top view shown in FIG. 1D.
Figure 1D:
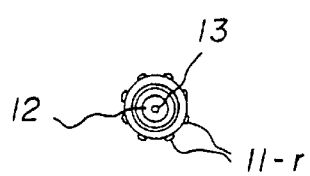

While the valve 10 of FIG. 1A has been shown enlarged for clarity, the invention contemplates miniaturization as indicated by the full-scale elevational view of FIG. 1C and the corresponding top view of FIG. 1D.

The annular sealing member 15 is an elastomeric O-ring having an outer diameter slightly larger than the inner diameter of the lower part 11-2, and encircles the lower portion of the spring 14. The probe 13 is hollow, desirably of the same material as the housing, and closed at its outer end 13-b, capping a hollow interior that extends outwardly to the outlet 11-o and communicates, in the upper part of the probe 13, with region between the probe and the member 12 by way of the slot 13-s.

While the sealing member 12, desirably elastomeric, is shown as being of a length shorter than the axial dimension of the housing 11, it may be elongated and incorporated functionally into the spring 14, which surrounds the co-axially mounted probe 13. The probe 13 is fixedly held, preferably by being integral with, and extending upwardly from the lower part 11-2. Like the tubular housing 11, the probe 13 can be formed of a moldable plastic, such as nylon.

Figure 2B:
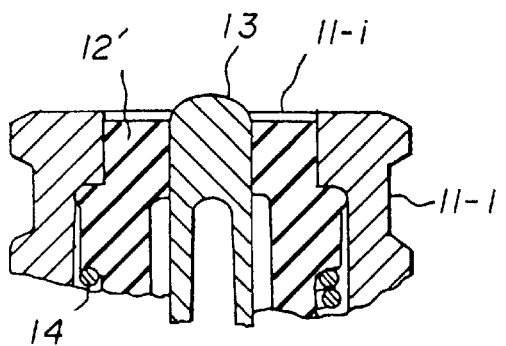
FIG. 2B is an alternative embodiment with a modified upper portion for the swabbable check valve of FIG. 1A.
Figure 2A:
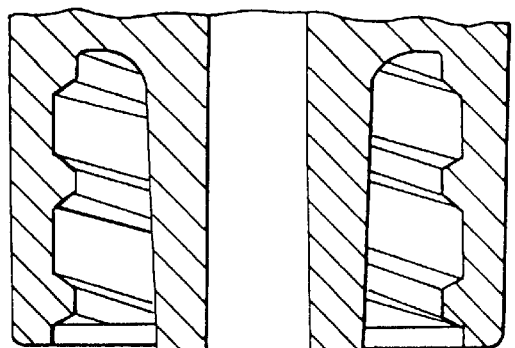
FIG. 2A is a partial view of the upper portion of the swabbable check valve of FIG. 1A.
Figure 2A:
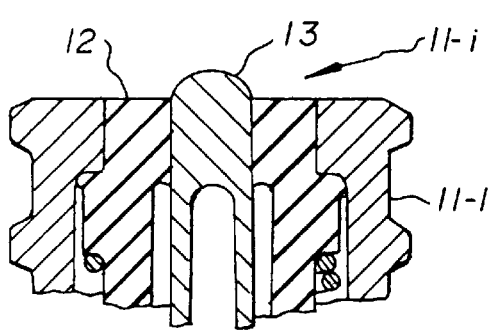
Figure 2C:
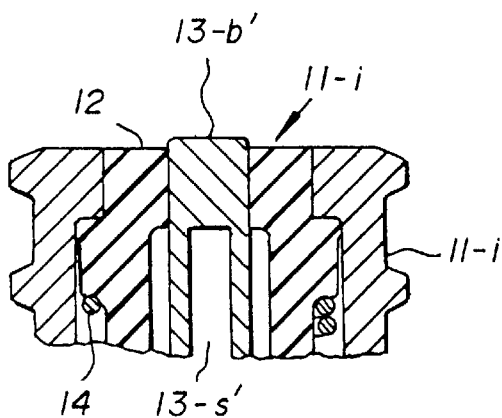
FIG. 2C is another alternative embodiment with a modified upper portion swabbable check valve of FIG. 1A.

Since the valve 10 is operated by an external member such as the Luer end of a syringe, the tip 13-b of FIG. 1A, which has been reproduced in FIG. 2A, serves as a fitment locator, of which FIG. 2A is merely representative. Although the outer end of the sealing member 12 is flush with the inlet 11-i in FIG. 2A, it may be depressed as shown for the member 12' in FIG. 2B, and the tip 13-b may be squared as illustrated by the tip 13-b' of FIG. 2C.

Figure 3A:
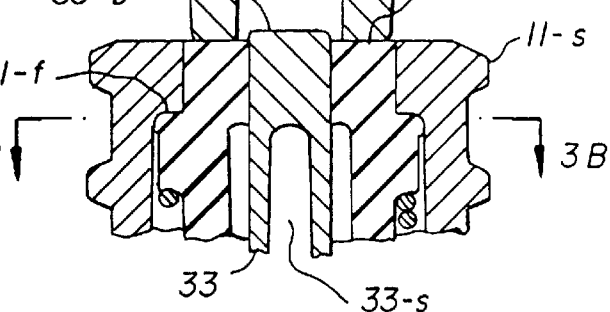
FIG. 3A shows the swabbable check valve of FIG. 2C being engaged by the Luer end of a syringe preparatory to needleless injection of fluid through the valve.
Figure 3B:
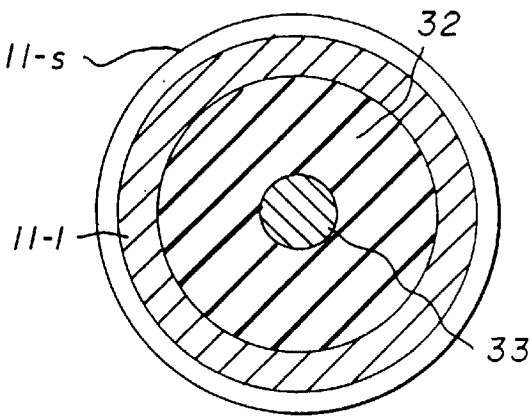
FIG. 3B is a sectional view of FIG. 3A, taken along the lines 3B—3B, illustrating the sealing of the inlet.

When the valve 10 is to be operated, an external member such as the male Luer outlet 38 of FIG. 3A is brought into contact with the sealing member 32, after being guided in position by the locator tip 33-b of the probe 33. It will be noted that the outlet 38 corresponds to the outlet 11-m of FIG. 1A and can take the form of the tip of a syringe. From an inspection of the cross-section shown in FIG. 3B, it will be apparent that the sealing member 32 provides a fluid-tight fit with the shoulder 31-f and with the outer unslotted end portion of the probe 33.

It also is evident that the sealing member 32 may be pushed or forced inwardly from its normal seating position. When forced inwardly as shown in FIG. 3C, the sealing member 32 extends below the transverse slot 33-s and thus establishes open communication for fluid through the housing 31 in either direction, e.g. inwardly or outwardly of the valve 30, as indicated by the double-headed arrows A.

The nature of the through-passage is illustrated by FIGS. 3D and 3E. In FIG. 3D the flow is confined to the slot 33-s and there is no flow in the interval I between the sealing member 32 and the housing 31. In FIG. 3E the flow is confined to the bore B, with no flow in the interval I' between the spring 34 and the housing 31, but with a seal being proved by the spring 34 bearing against a support ring 32-s of the member 32, establishing a seal of the member 32 against the probe 33.

The check valves 10 and 30 of the invention have a wide variety of uses, besides with catheters and the like. One such use is illustrated in cross-section in FIG. 4 where a valve substantially like the valve 10 of FIG. 1A has been incorporated into a "Y" site 40, that can be used, for example, in an IV (IntraVenous) procedure where the inlet branch IB of the Y site is connected to a container of saline solution that is fed through an outlet branch OB to a patient. The side branch SB of the site 40 can be used to inject medication into the patient. In prior practice the side branch SB channel C would be accessed through a needle actuated valve, but in the interest of avoiding needle sticks, needleless valves have been substituted. However, as noted above, the typical needleless valve has a long inlet channel in which contaminants and pathogens can accumulate.

Figure 4:
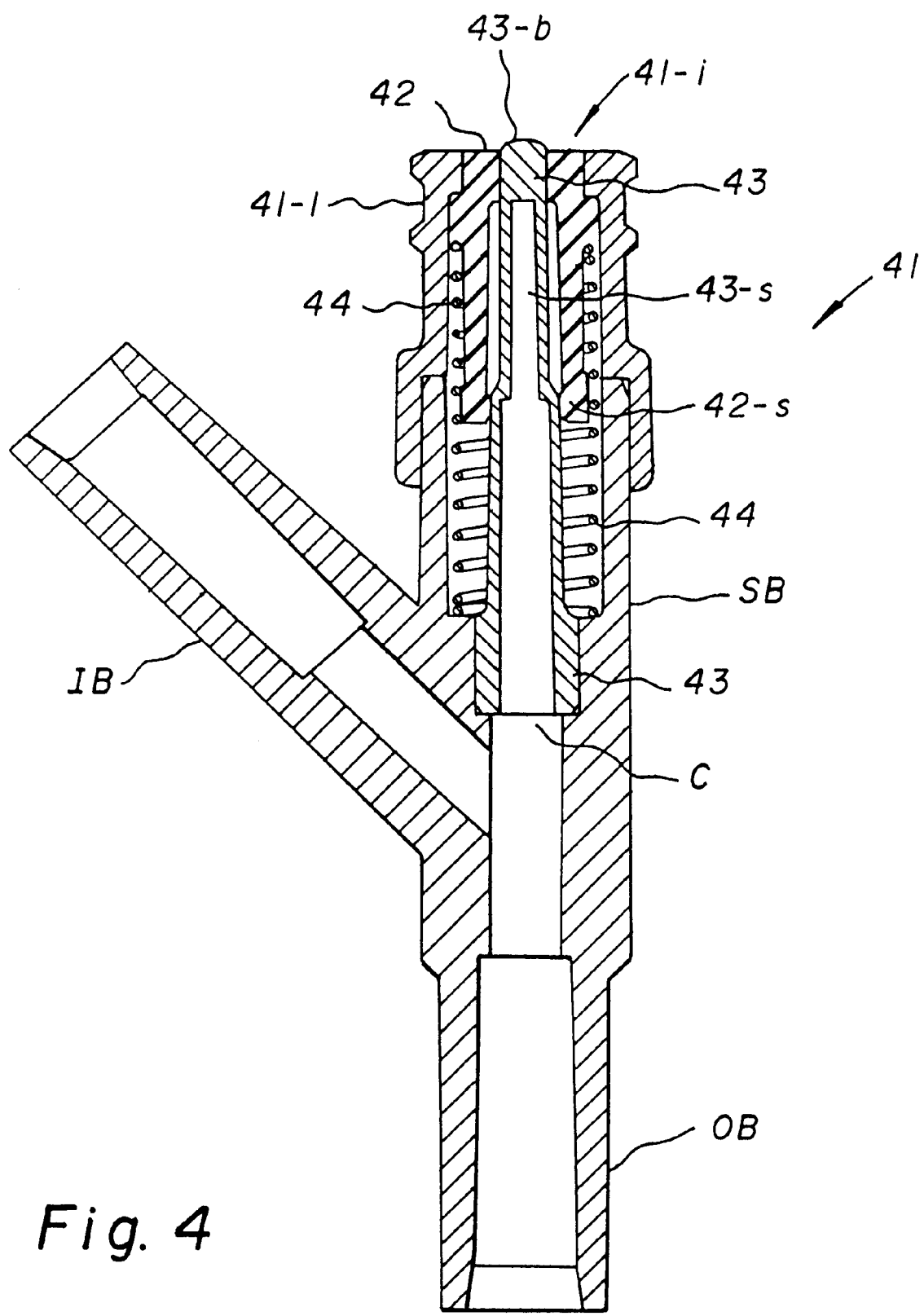
FIG. 4 is a sectional view of a "Y" site incorporating the swabbable check valve of the invention.

When the valve 10 of the invention is adapted to form the valve 41 of FIG. 4, the inlet 41-1 is swabbable by being wiped with a disinfectant so that when a Luer fitting is brought into contact with the sealing member 42, after being guided by the fitment 43-b, the desired medicament can be infused with reduced chance of contamination and no need to used a needle mounted syringe to make the injection. Parts 41-1, 42, 42-s, 43, 43-s and 44 correspond to the parts 11-1, 12, 12-s, 13, 13-s and 14 of FIG. 1A.

While preferred embodiments have been shown and described, it is to be understood that changes in details of construction and method from what has been illustrated may be made without departing from the spirit and scope of the invention as defined by the appended claims.

What is claimed:

1. Apparatus comprising a housing having an end with an input having connecting means and an entrance, and an output;
   a probe integral with said housing extending from said output to beyond said end of said input;
   said probe having a passageway thereinto connected to said output; and
   means sealing said input and substantially flush at said end with said entrance, surrounding said probe and depressible therealong to expose said passageway;
   wherein said entrance has a bore region of prescribed diameter, said sealing means terminates below said entrance and said connecting means is threaded;
   whereby the extension of said probe beyond said end of said input permits the swabbing thereof before the depression of the sealing means.

2. Apparatus as defined in claim 1 wherein said entrance has a prescribed level at said end, said sealing means terminates below said prescribed level and said connecting means is external to said housing.

3. Apparatus as defined in claim 1 wherein said housing is tubular, said probe is configured to facilitate swabbing and contact with means for depressing said sealing means.

4. Apparatus as defined in claim 3 wherein said probe terminates in a rounded end beyond said end of said input and said passageway is an axial slot.

5. Apparatus as defined in claim 1 wherein said sealing means includes means extending therealong for applying spring force thereto.

6. Apparatus comprising
   a housing having an end with an input and an output;
   a probe within said housing extending from said output to beyond said end of said input;
   said probe having a passageway thereinto connected to said output; and
   means sealing said input, surrounding said probe and depressible therealong to expose said passageway;
   whereby the extension of said probe beyond said end of said input permits the swabbing thereof before the depression of the sealing means, which has an intermediate region spaced from said probe;
   wherein said housing is tubular, said probe is configured to facilitate swabbing and contact with means for depressing said sealing means by terminating in an end beyond said end of said input.

7. Apparatus as defined in claim 6 wherein said sealing means seals to said housing at said end and to said probe at the base of said sealing means.

8. Apparatus as defined in claim 7 wherein said sealing means seals at a plurality of separated positions along said probe.

9. A method comprising the steps of:
   simultaneously molding a probe and a housing with an input having an end;
   sealing said end of said input by a depressible member surrounding said probe extending to said input; and
   depressing said member to uncover, in said probe, a passageway connected to an output;
   whereby the depression of said member permits flow from said input to said output;
   wherein said input has an entrance end having a prescribed level and said member is depressible from below said prescribed level which permits swabbing by disinfectant, followed by the infusion of medication.

10. The method as defined in claim 9 further including the step of contacting said probe above said end by means threaded to said input for depressing said sealing member.

11. The method as defined in claim 10 further including the step of contacting said probe at a rounded end beyond said end by means externally threaded to said input.

12. The method as defined in claim 10 further including the step of contacting said probe astride a flattened end beyond said end, and elongatedly surrounding said passageway in said probe.

13. The method as defined in claim 9 further including the step sealing to said probe between separate locations therealong with a non-sealing region therebetween.

14. The method as defined in claim 11 further including the step of applying spring force to and surrounding said sealing member.

15. Apparatus comprising a housing having an end with an input and a base with an output;

a probe within said housing terminating in said base and extending to beyond said end of said input;

said probe having a passageway thereinto connected to said output; and means sealing and seated at said input, surrounding said probe and depressible therealong to expose said passageway;

whereby the extension of said probe beyond said end of said input permits the swabbing thereof before the depression of the sealing means.

* * * * *